United States Patent [19]

Elliott et al.

[11] Patent Number: 4,504,491
[45] Date of Patent: Mar. 12, 1985

[54] PESTICIDES

[75] Inventors: Michael Elliott, Stevenage; Norman F. Janes, Luton; Bhypinder P. S. Khambay, Harrow Weald, all of England

[73] Assignee: National Research Development Corporation, London, England

[21] Appl. No.: 395,295

[22] Filed: Jul. 6, 1982

[30] Foreign Application Priority Data

Jul. 10, 1981 [GB] United Kingdom ............... 8121330

[51] Int. Cl.³ .................... A01N 37/34; A01N 37/00; C07C 121/50
[52] U.S. Cl. .................... 514/521; 514/531; 560/124; 560/101; 560/47; 560/48; 260/465 D
[58] Field of Search .................... 260/465 D; 560/124, 560/101, 47, 48; 424/304, 305, 308, 309

[56] References Cited

U.S. PATENT DOCUMENTS 4,024,163  5/1977  Elliott et al. ............... 260/465 D X
4,271,186  6/1981  Förster et al. .................... 424/304

FOREIGN PATENT DOCUMENTS 0050093  4/1982  European Pat. Off. .

Primary Examiner—Alan Siegel
Attorney, Agent, or Firm—Murray, Whisenhunt & Ferguson

[57] ABSTRACT

New pesticidal e.g. insecticidal, compounds are of formula

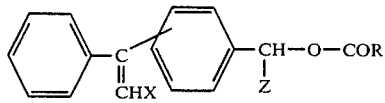

I wherein X represents hydrogen, halogeno or an alkyl group, Z represents hydrogen, an alkyl group or a cyano or ethynyl group and R represents the residue of a carboxylic acid RCOOH which is an acid forming a pesticidal compound when esterified with α-cyano-3-phenoxybenzyl alcohol.

The compounds can be prepared by conventional methods e.g. esterification.

7 Claims, No Drawings

PESTICIDES

DESCRIPTION

This invention relates to pesticides and is particularly concerned with new pesticidal compounds, their preparation, pesticidal compositions containing them and their pesticidal use.

Since the discovery in the 1940's of the structure of the naturally occurring pyrethrin insecticides, must research and development work has been directed to the production of synthetic analogues thereof. The naturally occurring insecticides are esters of certain cyclopropane carboxylic acids. Initially, investigations were directed to the production of new esters of the same cyclopropanecarboxylic acids from which the naturally occurring products are derived, but subsequently, investigations have been directed to esters in which the cyclopropane-carboxylic acid part of the molecule was modified and, more recently, it has been found that valuable insecticidal compounds can be prepared which are esters not of cyclopropane-carboxylic acids but which are esters of α-substituted phenyl acetic acids.

In developing new analogues of the naturally occurring insecticides, attention has been directed to the production of compounds having improved pesticidal properties while, at the same time, having an acceptably low level of toxicity to mammals, fish etc., and a sufficient level of physical stability so that the compounds can be used agriculturally, as well as for domestic and horticultural uses, without the need for repeated applications of the compound during a growing season.

We have now found that compounds of a new structural type have a particularly valuable combination of biological and physical properties rendering them useful as pesticidal compounds.

Accordingly, the present invention provides a compound of the general formula:

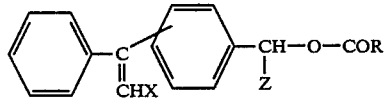

I wherein X represents hydrogen, halogeno or an alkyl group, Z represents hydrogen, an alkyl group or a cyano or ethynyl group and R represents the residue of a carboxylic acid RCOOH which is an acid forming a pesticidal compound when esterified with α-cyano-3-phenoxybenzyl alcohol.

The compounds of the present invention may be regarded, structurally, as esters of the new alcohol of formula V

V where X and Z are as defined above and alcohols of formula V, together with their ester-forming derivatives, form a further aspect of this invention.

In the compounds of formula I and V, it is preferred that X is hydrogen. When X is alkyl, it is preferred that this is an alkyl group containing 1 to 4 carbon atoms and is particularly a methyl group. When X is halogen, it is preferably chlorine but may also be bromine or fluorine.

In the compounds of formula I and V it is preferred that Z is H or CN.

It is also preferred that, in the compounds of formula I and V, that the 1-phenylvinyl or 1-phenyl-alkenyl or 1-phenylhalovinyl group be substituted at the 3-position on the benzyl ring.

In the compounds of formula I, R represents the residue of a carboxylic acid RCOOH which is an acid known to be capable of forming pesticidal compounds when esterified with α-cyano-3-phenoxybenzyl alcohol. There are a large number of carboxylic acids that are known to form pesticidal compounds of this type and these carboxylic acids fall, for the most part, into two clearly defined groups. The first group are the cyclopropane carboxylic acids which are the compounds where R is a group of the formula:

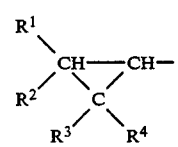

II

In formula II, $R^3$ and $R^4$ will normally be an alkyl group, usually the same alkyl group, containing 1 to 4 carbon atoms and, as is well-known in the art, dimethyl substitution normally gives high activity.

$R^2$ in formula II will normally be hydrogen or an alkyl group containing 1 to 4 carbon atoms and here, the experience of the art indicates that $R^2$ will usually be hydrogen for maximum activity except in those compounds where $R^1$ is also an alkyl group in which case $R^2$ preferably is an alkyl group, $R^1$, $R^2$, $R^3$ and $R^4$ all conveniently being the same alkyl group, e.g. methyl.

In formula II, $R^1$ can be hydrogen or a substituted or unsubstituted acyclic or carbocyclic group. When $R^1$ is an unsubstituted hydrocarbyl group, it can be a straight chain or branched saturated or unsaturated acyclic or carbocyclic group such as an alkyl group, an alkenyl or alkadienyl group or a cycloalkyl, cycloalkylalkyl or cycloalkylalkenyl group. These hydrocarbyl groups preferably contain up to 10, particularly up to 6 carbon atoms.

When group $R^1$ is substituted, it is preferably one of the hydrocarbyl groups mentioned above which is substituted by one or more halogeno groups which may be fluorine, chlorine or bromine or by an alkoxy or oximino group. When the substituents are two or more halogeno substituents, the halogeno substituents need not necessarily be the same halogen while when alkoxy groups are present, these preferably contain up to 4 carbon atoms and will normally be methoxy groups.

One particularly valuable structure for the group $R^1$ is of formula IV

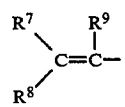

IV where $R^7$ and $R^8$, which may be the same or different, are each alkyl group containing 1 to 4 carbon atoms, a trifluoromethyl group or a halogeno group, which may be the same or different and are preferably fluorine, chlorine or bromine. One of $R^7$ and $R^8$ may also represent hydrogen or a phenyl or substituted phenyl group. Alternatively, $R^7$ and $R^8$ may together form a straight or branched substituted or unsubstituted saturated or unsaturated divalent hydrocarbon chain which may be substituted by one or more hetero atoms e.g. O, N or S, so that $R^7$ and $R^8$ together with the carbon atom to which they are attached forms a carbocyclic or heterocyclic ring which will preferably contain 5 to 7 ring atoms, optionally 1 or 2 carbon-to-carbon double bonds and optionally one or more alkyl ($C_1$–$C_4$) or halogeno substituents on the cycloaliphatic ring. Other compounds of interest are those in which R is a group of the structure

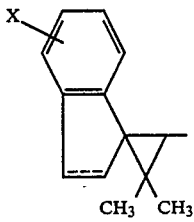

where the dotted line represents an optional double bond and X represents H or halogen such as chlorine.

Specific cyclopropane carboxylic acids from which the compounds I of the present invention may be structurally derived include the following:

Chrysanthemic acid including particularly (1R)-trans chrysanthemic acid;
Pyrethric acid;
Dimethylcyclopropane carboxylic acid;
Trimethylcyclopropane carboxylic acid;
Tetramethylcyclopropane carboxylic acid;
2,2-Dimethyl-3-(cyclopentylidenemethyl)cyclopropane carboxylic acid;
2,2-Dimethyl-3-(dibromovinyl)cyclopropane carboxylic acid; particularly the (1R)-cis isomer thereof;
2,2-Dimethyl-3-(dichlorovinyl)cyclopropane carboxylic acid, particularly the (1R)-cis isomer thereof,
2,2-Dimethyl-3-(1,2,2,2-tetrabromoethyl)cyclopropane carboxylic acid;
2,2-Dimethyl-3-(1,2-dibromo-2,2-dichloroethyl)cyclopropane carboxylic acid;
2,2-Dimethyl-3-(2-chloro-3,3,3-trifluoropropenyl)cyclopropane carboxylic acid;
2,2-Dimethyl-3-(tetrahydro-2-oxo-thien-3-ylidenemethyl)cyclopropane carboxylic acid.

The second major class of carboxylic acids from which the esters of formula I may be structurally derived are the α-substituted aryl acetic acid esters. In these compounds R in formula I will normally be of the structure III $$R^6-Ar-\underset{R^5}{\underset{|}{CH}}- \quad \text{III}$$

wherein Ar represents an aryl residue, $R^5$ represents a saturated or unsaturated straight chain or branched acyclic or cyclic hydrocarbon residue and $R^6$ represents hydrogen or one or more alkyl, alkoxy (including substituted alkoxy such as $OCF_3$ and $OCHF_2$) or halogeno substituents.

Ar will normally be an aryl residue based on a benzene ring although other aryl residues, e.g. polynuclear residues are also of interest. $R^5$ will normally be a saturated straight or branched chain hydrocarbon group, particularly an alkyl group containing up to 8 carbon atoms and it is often desirable that this alkyl group should contain at least one secondary carbon atom particularly when that secondary carbon atom is directly bonded to the carbon atom directly bonded to the $R^6$ substituted aryl group. Thus $R^5$ is preferably an isopropyl group or a secondary butyl group. $R^5$ can also be a cycloaliphatic residue, again preferably containing a secondary carbon atom located immediately adjacent to the carbon atom carrying the $R^6$ substituted phenyl group, e.g. $R^5$ may be a cyclopropyl group or an alkyl substituted cyclopropyl group. $R^5$ can also be a cycloalkylalkyl group.

$R^6$ is preferably one or more halogeno or halogen-containing substituents, e.g. F, Cl, Br or $OCHF_2$ or $OCF_3$ and, when more than one halogeno or halogen-containing substituent is present, they will normally be but are not necessarily the same halogen. When $R^6$ is an alkyl or alkoxy group, these preferably contain up to 4 carbon atoms and again, when more than one such group is present, they need not necessarily be the same groups. When only one substituent $R^6$ is present, it is preferably present in the para-position. When more than one $R^6$ substituent is present, the para-position is preferably substituted together with one or more of the ortho and meta positions.

Another class of carboxylic acids from which the esters of the present invention may be structurally derived are α-substituted arylamino acetic acids of the type $$R^6-Ar-NH-\underset{R^5}{\underset{|}{CH}}-COOH$$

where $R^5$, $R^6$ and aryl are as defined above.

Specific α-substituted phenyl acetic acids from which esters of the formula I may be structurally derived include:
α-Isopropyl-p-chlorophenyl acetic acid;
α-Cyclopropyl-p-chlorophenyl acetic acid;
α-Cyclopropyl-p-methylphenyl acetic acid;
α-Isopropyl-p-(difluoromethoxy)-phenyl acetic acid;
α-Isopropyl-(2-chloro-4-trifluoromethyl anilino) acetic acid.

The compounds of the invention may exhibit geometrical and/or optical isomerism. Compounds of the invention in which X represents alkyl or halogen can exist in the form of E or Z isomers in view of the asymmetric substitution on the carbon atoms linked by the olefinic bond and the present invention includes both the substantially pure E and substantially pure Z isomers as well as mixtures thereof.

Compounds of the invention in which Z represents $CH_3$, CN or ethynyl exhibit optical isomerism in that the carbon atom bearing the substituent Z can exist in the R or S configuration and the present invention includes compounds in which the configuration is substantially completely R or in which the configuration is substantially completely S or mixtures thereof.

Compounds of the invention in which R represents a substituted cyclopropane residue of formula II can exist in the form of both geometrical and optical isomers. This is because of the unsymmetrical substitution at $C_1$ and $C_3$ of the cyclopropane ring. Compounds of the present invention include those isomers in which the hydrogen atoms at $C_1$ and $C_3$ of the cyclopropane ring are substantially completely in the cis configuration or substantially completely in the trans configuration or mixtures thereof. The present invention also includes compounds in which the configuration at $C_1$ is substantially completely R or substantially completely S and mixtures thereof. In the compounds of the invention in which R represents a group of formula II, the optical configuration at $C_1$ and $C_3$ cannot vary independently of the geometrical configuration of the hydrogen atoms at $C_1$ and $C_3$ of the cyclopropane ring. The effect of this is that the configuration of the cyclopropane ring can be defined uniquely by specifying the optical configuration at $C_1$ and the geometrical configuration of the hydrogen atoms at $C_1$ and $C_3$ and, for definition purposes, we have adopted nomenclature of the form (1R)-cis, (1R)-trans etc. it being unnecessary to specify the optical configuration at $C_3$ which is fixed once the other two variables are defined. Adopting this nomenclature avoids the confusion which can arise by having to designate either R or S to the same optical configuration at $C_3$ depending upon the nature of the substituents on the cyclopropane ring and even those on the side chain.

When R is a group of formula II in which $R^1$ is a group of formula IV in which the substitution about the ethylenic bond is asymmetrical, that is to say $R^7 \neq R^8$ then the configuration of this part of the molecule can be substantially completely in the E form or substantially completely in the Z form or a mixture thereof.

When R is a group of formula III, the carbon atom to which $R^5$ is bonded can exist substantially completely in the S configuration or substantially completely in the R configuration or can be a mixture of the two forms.

The compounds of the present invention can be in the form of single isomers but, having regard to the fact that the compounds have at least one and frequently more than one centre of assymetry, the compounds of the invention will normally be in the form of isomer mixtures although these isomer mixtures can be optically active and/or substantially completely in one geometric form.

The compounds of the present invention can be prepared by reaction of alcohol IV or an esterifiable derivative thereof of formula

with a carboxylic acid or esterifiable derivative thereof of formula RCOQ where R, X and Z are as defined and Q and $Q^1$ are reactive groups that react together to form an ester linkage. It is usually convenient in practice either to react a salt of the carboxylic acid, e.g. a silver or triethylammonium salt with a benzylhalide derivative, that is to say a 1-phenylvinylbenzyl halide, but one can also react the acid or acid halide for example with the alcohol in the presence of suitable catalysts etc.

Alternatively, the esters of the invention can be prepared by transesterification by reacting a $C_1$–$C_6$ alkyl ester of the carboxylic acid with the benzyl alcohol of formula V in the presence of a basic trans-esterification catalyst. This method is not usually satisfactory where the molecule contains another base-sensitive residue, e.g. where the carboxylic acid is pyrethric acid.

The esters of the present invention may also be prepared by converting the carbonyl group in the corresponding benzoylbenzyl carboxylate of the formula

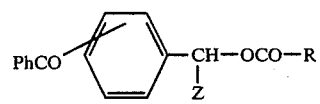

into a vinyl group either by a Wittig reaction or by the Grignard synthesis described below followed by dehydration.

The key intermediates to the synthesis of the pesticidal esters of the present invention are the new alcohols of formula V

The synthesis of the new alcohols can be achieved either by a Wittig reaction or by a Grignard reaction followed by dehydration to convert the carbonyl group in a benzoylbenzyl alcohol (possibly having a protected alcohol group) to form a 1-phenylvinyl benzyl alcohol having a protected alcohol group and then removing the protected alcohol group.

This synthesis produces alcohols of formula V in which Z=H.

Alcohols of the invention of formula V in which Z represents methyl, cyano or ethynyl are conveniently prepared via the corresponding benzaldehyde of formula VII

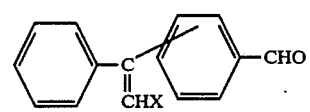

by reacting the aldehyde group with either methyl magnesium iodide or hydrogen cyanide or ethynyl magnesium bromide to give the methyl, cyano or ethynyl substituted benzyl alcohol.

The benzaldehyde of formula VII may be prepared from the corresponding methyl-substituted benzophenone. The methyl substituent is first subjected to side-chain bromination, e.g. by treatment with bromine and the resulting dibromomethyl benzophenone hydrolysed with strong mineral acid, e.g. sulphuric acid to give the corresponding benzoyl-benzaldehyde. The aldehyde group can then be protected, e.g. as an acetal or ketal and the unprotected carbonyl group linking the two aromatic rings then reacted with methyl magnesium iodide under the conditions of the Grignard synthesis followed by dehydration or reacted with a Wittig reagent to convert that carbonyl group into a corresponding 1-phenylvinyl benzaldehyde in which the aldehyde group is protected. The protecting group can then be removed to give the 1-phenylvinyl benzaldehyde which can then be reacted with methyl magnesium iodide, hydrogen cyanide or ethynyl magnesium bromide to give the correspondingly α-substituted 1-phenylvinyl benzyl alcohol. Protection of the aldehyde group is not necessary when, for example, an α-methyl-benzyl alcohol product is required. In such a case, a benzoyl-benzaldehyde can be reacted with 2 equivalents of, for example, methyl magnesium iodide in accordance with the reaction:

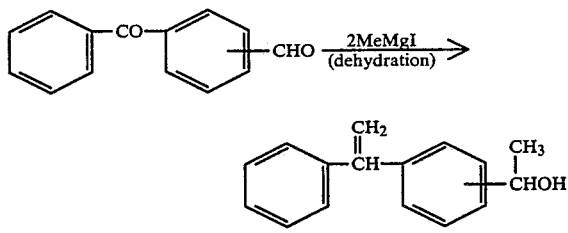

The Grignard technique can also be used directly on α-substituted benzoyl-benzoyl alcohols, e.g. in accordance with the reaction:

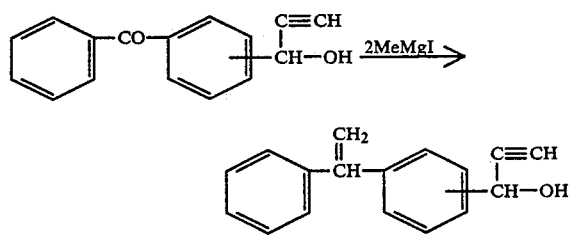

Any desired substitution on the 2-carbon atom of the vinyl group can be carried out by the procedures described above.

One or more of the pesticidal esters of formula I can be formulated with an inert carrier or diluent to give pesticidal compositions and such compositions form a further aspect of the present invention. These compositions can be in the form of dusts and granular solids, wettable powders mosquito coils and other solid preparations, or as emulsions, emulsifiable concentrates, sprays and aerosols and other liquid preparations after the addition of the appropriate solvents, diluents and surface-active agents.

The pesticidal compositions of the invention will normally contain from 0.001 to 25% by weight of the compound of formula I but the compositions can contain higher concentrations of active ingredient of formula I e.g. up to 95% for compositions to be sold as concentrates for dilution before use by the ultimate user.

The compositions of the invention can include diluents such as hydrocarbon oils, e.g. xylene or other petroleum fractions, water, anionic, cationic or non-ionic surface-active agents, anti-oxidants and other stabilisers as well as perfumes and colouring mattters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or of other types and the composition may also include synergists of the type known to be capable of synergising the activity of natural pyrethrin and pyrethroid-like insecticides. Synergists of this type include piperonyl butoxide, tropital and sesamex.

The compounds of formula I can be used to control pest infestation in the domestic, horticultural or agricultural or medical including veterinary areas. The compounds or compositions of the invention can be used to combat pest infestation by treating pests or surfaces or environments susceptible to pest infestation with effective amounts of the active compounds of formula I or of compositions containing them. For example, they may be used in a domestic environment for spraying rooms to combat infestation with houseflies or other insects, they can be used for treatment of stored dry crops or cereals to combat infestation by insects or other pests, they can be used to spray growing crops, e.g. cotton or rice to combat infestation by common pests and finally, they can be used in a medical or veterinary field, e.g. as a cattle spray to prevent or treat infestation by insects or other pests.

The following Examples are given to illustrate the invention. Temperatures are in °C.

EXAMPLE 1

3-(1-phenylvinyl)-benzyl(1R,trans)-chrysanthemate (a)

A mixture of 3-benzoylbenzyl alcohol (1.82 g, 5.0 mmol), dihydropyran (0.84 g, 10 mmol) and 'Amberlyst' 15 (0.4 g, 1.34 meq) in dry diethyl ether (60 cm$^3$) was stirred at room temperature for 1 hour. The resin was filtered off and the solvent and excess dihydropyran removed in vacuo. The residue (1.68 g (100%) was 2-(3-benzoylbenzyl)tetrahydropyran, n$_D^{20}$ 1.5672.

(b)

To a stirred suspension of methyltriphenylphosphonium iodide (5 g, 12.4 mmol) in dry ether (150 cm$^3$) under nitrogen at room temperature was added n-butyllithium in hexane (1.6M, 7.5 cm$^3$, 12 mmol) over 10 minutes. After 30 minutes the mixture was cooled in an ice bath and the product from (a) above (1.8 g, 6.1 mmol) in dry Et$_2$O (20 cm$^3$) was added dropwise and the mixture allowed to warm up to 20° C. over 3 hours. Water (200 cm$^3$) was added and the reaction mixture filtered after stirring for 10 minutes. The ethereal layer was separated off and the aqueous layer extracted twice with diethyl ether. The combined extracts were dried over anhydrous Na$_2$SO$_4$ and the solvent removed in vacuo. The residue was purified by HPLC on silica gel (Merck Lichroprep Si60, 15–25 μm, 100 g) eluted with 10% ether/petrol (60°–80°) to give 2-(3-(1-phenylvinyl)benzyl)tetrahydropyran. Yield 0.8 g (44.4%) n$_D^{20}$ 1.5712.

(c)

The product from (b) above (0.6 g, 2 mmol), 'Amberlyst' 15 (0.4 g, 1.34 meq) and methanol (20 cm$^3$) were stirred at 50° for 1 hour. After cooling to room temperature, the resin was filtered off and the solvent evaporated off in vacuo to give 3-(1-phenylvinyl)benzyl alcohol. Yield 0.42 g (97.7%) n$_D^{20}$ 1.5915.

(d)

(1R,cis)-chrysanthemic acid chloride (0.2 g, 0.63 mmol) was added to a stirred solution of the 3-(1-phenylvinyl)benzyl alcohol (0.15 g, 0.7 mmol) and pyridine (0.06 g, 0.7 mmol) at 20° C. After 4 hours, the mixture was passed through a column of alumina (10 g) and eluted with benzene (25 cm$^3$). The eluate was evaporated to dryness, finally at high vacuum and purified by tlc on silica to give 3-(1-phenylvinyl)benzyl(1R,- trans)chrysanthemate (Compound 1) (0.2 g 67%) $n_D^{20}$ 1.5604.

EXAMPLE 2

The procedure described in Example 1(d) was repeated but replacing the chrysanthemic acid chloride by (1R,cis)-2,2-dimethyl-3-(dibromovinyl)cyclopropane carboxylic acid chloride (dibromosanthemic acid) to give 3-(1-phenylvinyl)benzyl(1R,cis)-dibromosanthemate (Compound 2) $n_D^{20}$ 1.5986.

EXAMPLE 3

3-(1-phenylvinyl)benzaldehyde (a)

A solution of 3-methylbenzophenone (10 g, 51 mmol) in CCl$_4$ (40 cm$^3$) was refluxed with stirring and illuminated with an infra-red heat lamp (275 w) while bromine (16.3 g, 102 mmol) in CCl$_4$ (50 cm$^3$) was added dropwise. After 16 hours the clear solution was washed successively with water, saturated sodium bicarbonate, water and saturated sodium chloride. After drying the solution, the solvent was removed under vacuo to give 3-dibromomethylbenzophenone. Yield 17.3 g (96%), 98% purity.

(b)

Concentrated sulphuric acid (14.5 cm$^3$) was added to a stirred mixture of the dibromide obtained in (a) above (9.65 g, 27.3 mmol) in water (0.7 cm$^3$) and heated initially to 70° C. and then to 110° C. whilst under reduced pressure (20 mmHg) with an air bleed. After 90 minutes, the mixture was cooled, poured onto ice and after warming to 20° C., extracted with diethyl ether (200 cm$^3 \times 3$). The combined extracts were washed with saturated sodium bicarbonate, water and saturated sodium chloride. After drying with anhydrous Na$_2$SO$_4$, the solvent was evaporated off and the residue distilled to give 3-benzoylbenzaldehyde. Yield 4.8 g (84%) b. pt. 140°–150°/0.04 mmHg.

(c)

To a stirred solution of benzoylbenzaldehyde (2 g, 10 mmol) and 1,2-bis-(trimethoxysiloxy)ethane (2.3 g, 11 mmol) in dry dichloromethane (30 cm$^3$) under N$_2$ at room temperature was added trimethylsilylmethyl trifluoromethanesulphonate (5 drops). After stirring at 20° C. for 48 hours, pyridine (3 drops) was added followed by saturated NaHCO$_3$ (20 cm$^3$) and diethyl ether (20 cm$^3$). The resulting mixture was stirred for 30 minutes. The ethereal layer was separated off and the aqueous layer extracted twice more with diethyl ether. The combined extracts were washed with water, dried over a mixture of anhydrous Na$_2$CO$_3$ and anhydrous Na$_2$SO$_4$ (1:1) and the solvent removed in vacuo to give 2-(3-benzoylphenyl)-1,3-dioxolane, $n_D^{20}$ 1.5890. Yield 2.2 g (91.7%).

(d)

To a stirred suspension of methyltriphenylphosphonium iodide (5 g, 12.4 mmol) in dry ether (150 cm$^3$) under nitrogen at room temperature was added n-butyllithium in hexane (15% w/w, 5 g) over 15 minutes. After 30 minutes, the mixture was cooled in an ice bath and the dioxolane from (c) above (1.8 g, 7.1 mmol) dissolved in dry diethyl ether (10 cm$^3$) was added dropwise. The cooling bath was removed and the mixture allowed to warm up to 20° C. over 3 hours. Water (200 cm$^3$) was added to the reaction mixture and filtered after stirring for 10 minutes. The ethereal layer was separated and the aqueous layer extracted twice with ether. The combined extracts were dried over anhydrous Na$_2$SO$_4$ and the solvent removed in vacuo to give 2-(3-(1-phenylvinyl)phenyl)-1,3-dioxolane. Yield 1.54 g.

(e)

The crude product from (d) above (1.54 g) was added to 10% H$_2$SO$_4$ (15 cm$^3$) in tetrahydrofuran (15 cm$^3$) and refluxed for 1 hour, cooled and poured onto water (200 cm$^3$), then extracted with dichloromethane ($\times$3). The combined extracts were dried and evaporated in vacuo. The product was purified by passing through a short column of silica gel eluting with ether to give 3-(phenylvinyl)benzaldehyde. Yield 0.77 g (60%). $n_D^{20}$ 1.6148.

(f)

A mixture of the aldehyde from (e) above (0.77 g, 21 mmol), THF (10 cm$^3$) sodium cyanide (0.6 g) and water (3 cm$^3$) was stirred in an ice-bath and 40% sulphuric acid (1.8 cm$^3$) added dropwise whilst maintaining the temperature below 5° C. After 1 hour, the cooling bath was removed and the mixture allowed to warm up to 20° over 1 hour. The mixture was poured onto water (200 cm$^3$) and extraced with carbon tetrachloride (50 cm$^3 \times 3$). The combined extracts were washed with water, dried and the solvent evaporated off to give α-cyano-3-(1-phenylvinyl)benzyl alcohol. Yield 0.8 g (87%) $n_D^{20}$ 1.5935.

(g)

The esterification procedure described in Example 1(d) and 2 was repeated using the alcohol obtained in paragraph (f) above to give α-cyano-3-(1-phenylvinyl)-benzyl(1R,trans)chrysanthemate (Compound 7) $n_D^{20}$ 1.5628 and α-cyano-3-(1-phenylvinyl)benzyl(1R-cis)dibromosanthemate (Compound 8) $n_D^{20}$ 1.5872.

EXAMPLE 4

(a) α-Ethynyl-3-benzoylbenzyl alcohol

Ethynylmagnesium bromide (11.2 mmol) in tetrahydrofuran (20 cm$^3$) was added dropwise to a stirred solution of 3-benzoylbenzaldehyde (2 g, 9.5 mmol, prepared as in Example 3(b) in tetrahydrofuran (30 cm$^3$) through which purified acetylene was being passed. After 2 hours, saturated ammonium chloride solution (200 cm$^3$) was added, and the mixture extracted with ether (3$\times$50 cm$^3$). The combined extracts were washed with saturated sodium chloride, dried over anhydrous sodium sulphate, and the solvent removed in vacuo. The product was purified by thin layer chromatography on silica to give the title alcohol, yield 1.1 g (49%) $n_D^{20}$ 1.6075.

(b) α-Ethynyl-3-(1-phenylvinyl)benzyl alcohol

To methyl magnesium iodide (1.4 g) in ether (25 cm$^3$) was added a solution of α-ethynyl-3-benzoylbenzyl alcohol (0.5 g) in ether (10 cm$^3$) with stirring during 10 minutes at 20° C., then the mixture refluxed for 5 minutes and poured onto a mixture of 40% sulphuric acid (40 cm$^3$), sodium thiosulphate (3 g) and tetrahydrofuran (20 cm$^3$). After 16 hours at 20° C., this mixture was extracted with ether (3$\times$150 cm$^3$), washed with sodium thiosulphate solution (2M), saturated sodium chloride, dried and finally evaporated to give the title product, yield 0.48 g (96%) $n_D^{20}$ 1.5942.

(c) The procedure described in Example 1(d) and 2 was repeated using α-ethynyl-3-(1-phenylvinyl)benzyl alcohol in place of 3-(1-phenylvinyl)benzyl alcohol to give the α-ethynyl-3-(1-phenylvinyl)benzyl ester of (1R,trans)chrysanthemic acid, (Compound 5) $n_D^{20}$ 1.5568 and (1R,cis)dibromosanthemic acid (Compound 6) $n_D^{20}$ 1.5965.

EXAMPLE 5

(a) 3-(1-Phenyl-2-chlorovinyl)benzyl alcohol

To a stirred suspension of (chloromethyl)triphenyl phosphonium chloride (2 g, 5.8 mmol) in ether (25 cm$^3$) containing piperidine (0.51 g, 6 mmol) at 20° C. was added butyl lithium (15%, 2.4 g, 5.6 mmol) in hexane over 15 minutes and then kept for 2 hours to generate the chloromethylene phosphorane. The mixture was cooled to −78° C., and 3-benzoylbenzyl acetate (1 g, 3.9 mmol, prepared from the alcohol and acetyl chloride by the esterification procedure of Example 1(d)) in ether (10 cm$^3$) was added dropwise. After 1 hour at −78° C. and 24 hours at 20° C., water (100 cm$^3$) was added with stirring, and the mixture filtered. The ether layer, and extracts of the aqueous layer were combined, dried over anhydrous Na$_2$SO$_4$ and evaporated to dryness. After purification by t.l.c. on silica, the 3-(1-phenyl-2-chlorovinyl)benzyl acetate, yield 0.26 g (23%) had $n_D^{20}$ 1.5912.

The above acetate (0.25 g, 0.9 mmol) in ether (20 cm$^3$) was reduced by adding lithium aluminium hydride (0.05 g, 1.4 mmol) and stirring at 20° C. for 1 hour. Water (0.05 cm$^3$) was added, followed by 15% aqueous sodium hydroxide (0.05 cm$^3$) and water (0.15 cm$^3$). After stirring a further 10 minutes, the solution was filtered, and the filtrate evaporated in vacuo to give 3-(1-phenyl-2-chlorovinyl)benzyl alcohol, yield 0.21 g (98%) $n_D^{20}$ 1.6200.

(b)

The procedure described in Example 1(d) and 2 was repeated using 3-(1-phenyl-2-chlorovinyl)benzyl alcohol in place of 3-(1-phenylvinyl)benzyl alcohol to give the 3-(1-phenyl-2-chlorovinyl)benzyl ester of (1R,trans)chrysanthemic acid (Compound 11) $n_D^{20}$ 1.5706 and (1R,cis)dibromosanthemic acid (Compound 12) $n_D^{20}$ 1.5962.

EXAMPLE 6

3-(1-Phenylprop-1-enyl)benzyl alcohol

This alcohol $n_D^{20}$ 1.5725 was prepared by the procedure of Example 5(a) using the phosphorane generated from ethyltriphenylphosphonium iodide with butyllithium. The alcohol was then esterified with (1R,trans)-chrysanthemic acid and (1R,cis)-dibromosanthemic acid by the procedure described in Examples 1(d) and 2 to give 3-(1-phenylprop-1-enyl)benzyl (1R,trans)chrysanthemate, (Compound 9) $n_D^{20}$ 1.5618 and (1R,cis)dibromosanthemate, (Compound 10) $n_D^{20}$ 1.5978.

EXAMPLE 7

(a) α-Methyl-3-(1-phenylvinyl)benzyl alcohol

To methyl magnesium iodide (from magnesium and methyl iodide (2.9 g) in ether (10 cm$^3$)), was added 3-benzoylbenzaldehyde (1 g, 4.8 mmol, prepared as in Example 3(b)). After refluxing for 10 minutes, the mixture was cooled, poured onto dilute sulphuric acid and extracted with ether (3×200 cm$^3$). The extract was washed with solutions of sodium thiosulphate and sodium chloride, then dried (anhydrous Na$_2$SO$_4$) and evaporated to a residue which was dissolved in a mixture of tetrahydrofuran (10 cm$^3$) and 40% sulphuric acid (10 cm$^3$) for 10 hours. The mixture was poured onto water, and extracted with dichloromethane (3×50 cm$^3$). The extract was dried and evaporated to give the title alcohol. Yield 1.05 g (98%) $n_D^{20}$ 1.5978.

(b)

The procedure described in Examples 1(d) and 2 was repeated using α-methyl-3-(1-phenylvinyl)benzyl alcohol in place of 3-(1-phenylvinyl)benzyl alcohol to give the α-methyl-3-(1-phenylvinyl)benzyl ester of (1R,trans)chrysanthemic acid (Compound 3) $n_D^{20}$ 1.5588 and of (1R,cis)dibromosanthemic acid (Compound 4) $n_D^{20}$ 1.5912.

EXAMPLE 8

Compounds 3–8 described above are mixtures of compounds with R and S configuration at C$_α$. One of the components of Compound 8, described in Example 3(g), was isolated by dissolving Compound 8 in a minimum amount of a 10/90 by volume mixture of diethylether/60° C. to 80° C. petroleum ether at 20° C. and then cooling the solution to below 0° C. until a crystalline product separated. The crystalline product was filtered from the mother liquor and was found to have an m.p. of 95° to 96° C. This crystalline material was a single isomer (Compound 13) believed to have S configuration at C$_α$ so that it was S-α-cyano-3-(1-phenylvinyl)benzyl(1R,cis)3-(2,2-dibromovinyl)-2,2-dimethylcyclopropane carboxylate.

The pesticidal activity of esters of formula I of the invention was assessed against houseflies and mustard beetles using the following techniques:

Houseflies (*Musca domestica*)

Female flies were treated on the thorax with a one microliter drop of insecticide dissolved in acetone. Two replicates of 15 flies were used at each dose rate and 6 dose rates were used per compound under test. After treatment, the flies were maintained at a temperature of 20° C. ±1° and kill was assessed 24 and 48 hours after treatment. LD$_{50}$ values were calculated in micrograms of insecticide per fly and relative toxicities were calculated from the inverse ratios of the LD$_{50}$ values (see Sawicki et al, Bulletin of the World Health Organisation, 35, 893, (1966) and Sawicki et al, Entomologia and Exp. Appl. 10, 253, (1967)).

Mustard Beetles (*Phaedon cochleariae Fab*)

Acetone solutions of the test compound were applied ventrally to adult mustard beetles using a micro drop applicator. The treated insects were maintained for 48 hours after which time kill is assessed. Two replicates of 40 to 50 mustard beetles were used at each dose level and 5 dose levels were used for each compound. Again, LD$_{50}$ values were calculated and relative toxicities were calculated for the inverse ratios of LD$_{50}$ (see Elliott et al, J. Sci. Food Agric. 20, 561, (1969)).

Relative toxicities were calculated by comparison with 5-benzyl-3-furylmethyl(1R)-trans-chrysanthemate (Bioresmethrin) which is one of the more toxic chrysanthemate esters known to houseflies and mustard beetles, its toxicity being about 24 times that of allethrin to houseflies and 65 times that of allethrin to mustard beetles.

The following relative toxicities were recorded.

Relative Toxicity

| Compound | X | Z | R⁷/R⁸ | Houseflies | Mustard Beetles |
|---|---|---|---|---|---|
| Bioresmethrin | | | | 100 | 100 |
| 1 | H | H | H | 2 | 5 |
| 2 | H | H | Br | 25 | 9 |
| 3 | H | CH₃ | H | 0.3 | 0.2 |
| 4 | H | CH₃ | Br | 2 | 2 |
| 5 | H | C≡CH | H | 1 | 2 |
| 6 | H | C≡CH | Br | 2 | 7 |
| 7 | H | CN | H | 4 | 4 |
| 8 | H | CN | Br | 9 | 10 |
| 9 | CH₃ | H | H | NT | 1 |
| 10 | CH₃ | H | Br | 2 | 9 |
| 11 | Cl | H | H | NT | 0.3 |
| 12 | Cl | H | Br | 1 | 3 |
| 13 | H | CN | Br | 68 | 34 |

NT = not tested

Compounds of formula I may be formulated as the active compound or as one of the active compounds in pesticidal compositions as described in the Formulation Examples below.

Formulation 1
Oil-based liquid spray for household insects

| | |
|---|---|
| active compound | 0.015% w/v |
| 25% Pyrethrum Extract | 0.25% |
| Piperonyl butoxide | 0.5% |
| Antioxidant | 0.1% |
| Odourless light oil solvent e.g. xylene to make 100 vols. | |

Formulation 2
Water-based liquid spray concentrate for mosquito control

| | |
|---|---|
| active compound | 0.25% w/v |
| Piperonyl butoxide | 1.0% |
| Non-ionic emulsifier | 0.25% |
| Antioxidant | 0.1% |
| Water to make | 100 vols. |

This concentrate should be diluted e.g. 1:80 v/v with water, before spraying.

Formulation 3
Aerosol

| | |
|---|---|
| active compound | 0.05% |
| 25% Pyrethrum Extract | 0.8% |
| Piperonyl butoxide | 1.5% |
| Odourless petroleum distillate (b.p. 200–265°) | 17.338% |
| Propellant, e.g. a mixture of equal quantities of trichloromonofluoromethane and dichlorodifluoromethane | 80.0% |
| Perfume | 0.2% |
| Antioxidant | 0.1% |

Formulation 4
Mosquito coil

| | |
|---|---|
| active compound | 0.25% |
| Tabu powder (also known as pyrethrum marc) | 30.0% |
| Filler(s), e.g. wood flour, powdered leaves or nut shells | 68.75% |
| Brilliant Green (dyestuff) | 0.5% |
| p-Nitrophenol | 0.5% |

Formulation 5
Emulsifiable concentrate

| | |
|---|---|
| active compound | 1.5% w/w |
| Non-ionic emulsifier | 25.0% |
| Xylene | 73.4% |
| Antioxidant | 0.1% |

This concentrate may then be diluted at the rate of 30 mls. to 4½ liters of water prior to use.

Formulation 6
General purpose powder for household, garden, livestock or grain storage use

| | |
|---|---|
| active compound | 0.05% w/w |
| Tropital (the synergist piperonyl-bis-2-[2'-n-butoxyethoxy]ethyl acetal | 0.25% |
| Antioxidant, e.g. butyl hydroxy toluene or butyl hydroxy anisole | 0.03% |
| Filler | 99.67% |

We claim:

1. A compound of the general formula:

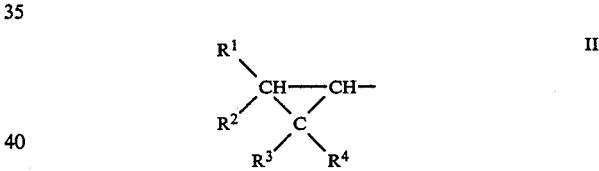

wherein X represents hydrogen, halogeno or an alkyl group, Z represents hydrogen, an alkyl group or a cyano or ethynyl group and R represents a group of the formula:

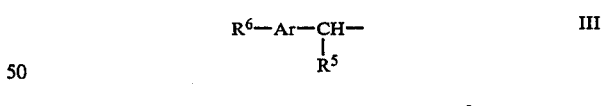

wherein $R^1$ represents hydrogen or a substituted or unsubstituted acyclic or carbocyclic group, $R^2$ represents hydrogen or an alkyl group and $R^3$ and $R^4$ each represent an alkyl group; or a group of formula:

$$R^6-Ar-\underset{\underset{R^5}{|}}{CH}-$$  III wherein Ar represents an aryl residue, $R^5$ represents a saturated or unsaturated straight chain or branched acyclic or cyclic hydrocarbon residue and $R^6$ represents hydrogen or one or more alkyl, alkoxy, $OCF_3$, $OCHF_2$ or halogeno substituents; or a group of the formula:

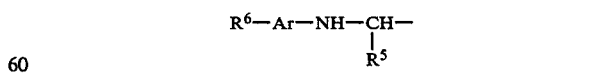

wherein $R^5$, $R^6$ and Ar are as defined above.

2. A compound according to claim 1, wherein $R^1$ represents an isobutenyl or 2,2-dibromovinyl group, $R^2$ represents hydrogen and $R^3$ and $R^4$ each represent methyl.

3. A compound according to claim 1 wherein the acid has (1R,cis) configuration.

4. A compound according to claim 1 wherein Z represents H or CN and X represents H, CH$_3$ or Cl.

5. A pesticidal composition comprising a compound according to claim 1 together with an inert diluent or carrier.

6. A method of pest control which comprises applying to a pest or to a surface or environment susceptible to pest attack a compound according to claim 1 or a composition according to claim 5.

7. A compound according to claim 1 or 3 which is α-cyano-3-(1-phenylvinyl)benzyl 3-(2,2-dibromovinyl)-2,2-dimethylcyclopropanecarboxylate.

* * * * *